United States Patent
Rhee et al.

(10) Patent No.: US 9,635,860 B2
(45) Date of Patent: May 2, 2017

(54) ANTIMICROBIAL COMPOSITION INCLUDING PHYTIC ACID AND ELECTROLYTES

(71) Applicant: Korea University Research and Business Foundation, Seoul (KR)

(72) Inventors: Min-Suk Rhee, Gyeonggi-do (KR); Nam-Hee Kim, Gyeonggi-do (KR)

(73) Assignee: Korea University Research and Business Foundation, Seoul (KR)

( * ) Notice: Subject to any disclaimer, the term of this patent is extended or adjusted under 35 U.S.C. 154(b) by 0 days.

(21) Appl. No.: 15/064,921

(22) Filed: Mar. 9, 2016

(65) Prior Publication Data

US 2017/0000134 A1    Jan. 5, 2017

(30) Foreign Application Priority Data

Jul. 1, 2015 (KR) .................. 10-2015-0094098
Oct. 23, 2015 (KR) .................. 10-2015-0147975

(51) Int. Cl.
*A01N 59/08* (2006.01)
*A01N 57/12* (2006.01)

(52) U.S. Cl.
CPC ............. *A01N 59/08* (2013.01); *A01N 57/12* (2013.01)

(58) Field of Classification Search
None
See application file for complete search history.

(56) References Cited

U.S. PATENT DOCUMENTS

| 4,647,458 A * | 3/1987 | Ueno ............... A01N 37/02 422/28 |
| 6,599,440 B2 * | 7/2003 | Hartley ............. C09K 3/185 106/13 |

FOREIGN PATENT DOCUMENTS

| CN | 103156243 A | * | 6/2013 |
| KR | 10-1998-0013754 A | | 5/1998 |

OTHER PUBLICATIONS

Bari, M. L., et al. "Combined efficacy of nisin and pediocin with sodium lactate, citric acid, phytic acid, and potassium sorbate and EDTA in reducing the Listeria monocytogenes population of inoculated fresh-cut produce." Journal of Food Protection® 68.7 (2005): 1381-1387.*
Thomas, Linda V., and J. W. Wimpenny. "Investigation of the effect of combined variations in temperature, pH, and NaCl concentration on nisin inhibition of Listeria monocytogenes and *Staphylococcus aureus*." Applied and Environmental Microbiology 62.6 (1996): 2006-2012.*
Davidson P, Taylor T, Schmidt S. 2013. Chemical Preservatives and Natural Antimicrobial Compounds, p. 765-801. In Doyle M, Buchanan R (ed), Food Microbiology. ASM Press, Washington, DC. doi: 10.1128/9781555818463.ch30.*
Kim, N.H. et al, "Phytic Acid and Sodium Chloride Show Marked Synergistic Bactericidal Effects against Nonadapted and Acid-Adapted *Escherichia coli* O157:H7 Strains", Applied and Environmental Microbiology, vol. 82, No. 4, (Feb. 2016), pp. 1040-1049.

* cited by examiner

*Primary Examiner* — Kevin S. Orwig
*Assistant Examiner* — Peter Anthopolos
(74) *Attorney, Agent, or Firm* — Mintz Levin Cohn Ferris Glovsky and Popeo, P.C.; Kongsik Kim; Linyu L. Mitra

(57) ABSTRACT

The present invention relates to an antimicrobial composition including phytic acid and electrolytes.

1 Claim, 6 Drawing Sheets

FIG. 4

ANTIMICROBIAL COMPOSITION INCLUDING PHYTIC ACID AND ELECTROLYTES

CROSS-REFERENCE TO RELATED APPLICATIONS

This application claims priority to Korean Application No. 10-2015-0094098 filed on Jul. 1, 2015 and Korean Application No. 10-2015-0147975 filed on Oct. 23, 2015, which applications are incorporated herein by reference.

TECHNICAL FIELD

The present invention relates to an antimicrobial composition including phytic acid and electrolytes.

BACKGROUND

Inositol hexaphosphoric acid, a main component of phytic acid, is a light yellow- or brown-colored syrup state liquid, and is known to be odourless. Structurally, inositol hexaphosphoric acid is a material having inositol as a basic structural body bonding to 6 phosphoric acid ($H_2PO_4$) with 12 hydroxyl groups, and thereby having a relatively high molecular weight of 660.03 g/mol.

Phytic acid performs a role of a phosphoric acid storehouse in most plant bodies, and is widely distributed in various plant bodies such as beans, tree fruits and grain hulls. Accordingly, phytic acid may be separated and purified using a waste such as hulls and skins generated when producing processed vegetable foods gone through simple processing such as selecting, molting, cutting and washing, and various technologies for increasing the yield have been actually developed from various plant bodies. Among vegetable crops, a typical plant used for separating and purifying phytic acid is rice, and rice bran among rice. Rice is a major crop widely consumed in the Asia regions, and six million tons of rice is annually produced worldwide, and only endosperm corresponding to approximately 70% of rice is taken as a grain, and the remaining rice husk (approximately 20%), rice bran (approximately 8%), rice germ (approximately 2%) and the like are inevitably produced as by-products. Phytic acid is a nature-derived material capable of being obtained in non-edible parts (husk, inside skin and the like) of not only rice, but beans or nut products such as beans, walnuts, pine nuts and peanuts in 1 to 9% yield, and studies on the economic availability thereof have been required.

Phytic acid in the fields of beauty cares, medicines and foods has been used as antioxidants, anti-cancer materials (colorectal cancer suppressing function), antiobesity drugs (fatty acid suppressing function), renal stone medicines (mineral chelating function) and the like, and particularly in the field of beauty cares, products commercialized in various concentrations and ratios have been in the market for preventing acne or skin troubles. In the field of food industry, when phytic acid-containing food is taken, the phytic acid adsorbs vital minerals such as calcium, iron, zinc and potassium, and forms insoluble complex in the body, and is determined as an antinutrient with reports of nonnutritive metabolism such as vital mineral utility and protein absorption decline in the body. In Korea, phytic acid is listed as a food additive (natural additive 91), and is normally used in canned foods, beverages, fermented foods, fish meat pastes and noodles as a fermentation agent and a chelating agent, and is used as a struvite inhibitor and a darkening inhibitor in marine product canned foods.

Meanwhile, Enterohemorrhagic *Escherichia coli* (EHEC) is a representative food poisoning bacteria brought into a human digestive organ, and causing serious food poisoning by producing verotoxins and inducing intestinal hemorrhage, and is highly toxic having an infective dose of 100 or less per g or ml, and may cause complications such as hemolytic uremic syndrome and thrombotic thrombocytopenia leading to early treatment failure. EHEC is normally discovered in animals, and particularly in intestines of cattle, and as a result, food poisoning occurs due to EHEC infection from under-cooked meat or processed meat product intake, or due to the intake of fresh foods cross-contaminated from contaminated animal food materials or food processing place surfaces. Particularly, EHEC has strong resistance to acid, and is counted as a main cause of food poisoning related to acid foods of pH 4.5 or lower such as apple juice, cucumber pickles and mustard sauce, and has been reported to induce acid adaptation when exposed to acidic environments for a long time causing an increase for acid resistance, and accordingly, new technologies for effectively disinfecting and controlling EHEC has been required.

Despite sufficient potential of phytic acid as a natural antimicrobial agent, there have been almost no advanced development cases on antimicrobial agents having phytic acid as a main component. Korean Patent Application Laid-Open Publication No. 1998-0013754 discloses an antimicrobial composition having phytic acid as a main component, however, this is for disinfecting and algiciding algae and layer farming inhibition bacteria living in sea water and fresh water, and when used for food poisoning bacteria, not only the effects are expected to be insignificant, but there is also a limit in that excessive phytic acid needs to be used.

Accordingly, technologies with phytic acid having excellent potential as a natural antimicrobial agent as a main component, and capable of effectively controlling bacteria such as acid resistant EHEC with a small phytic acid amount have been required.

SUMMARY

An object of the present invention is to provide an antimicrobial composition capable of maximizing bactericidal activity of individual materials while preventing overuse of phytic acid or electrolytes, and particularly, capable of effectively disinfecting and controlling bacteria such as acid resistant EHEC.

In view of the above, an aspect of the present invention provides an antimicrobial composition including phytic acid and electrolytes.

BRIEF DESCRIPTION OF THE DRAWINGS

The objects and qualities of the present invention will become apparent from the following description of embodiments given in conjunction with the accompanying drawings, in which:

FIG. 4 shows comparison of bactericidal activity of phytic acid or an aqueous sodium chloride solution, and a mixture composition thereof (treated for 5 minutes);

DETAILED DESCRIPTION

Figure 1:
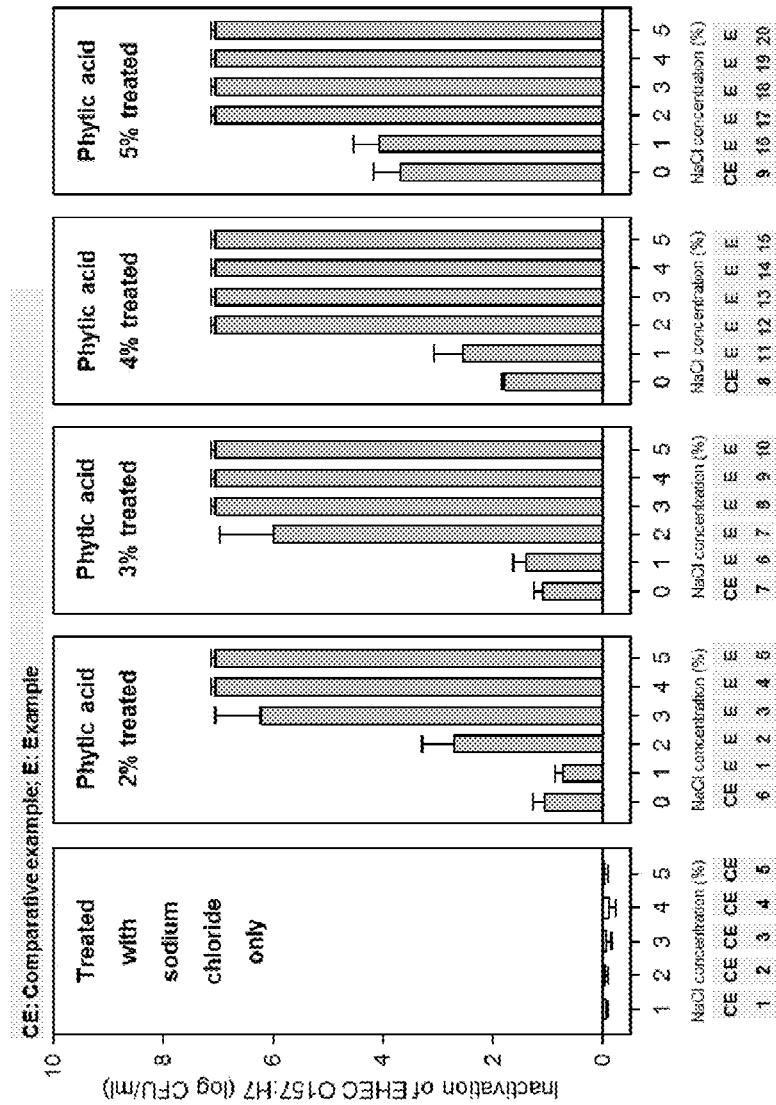
FIG. 1 shows comparison of bactericidal activity of phytic acid or an aqueous sodium chloride solution, and a mixture composition thereof (treated for 1 minute)

Hereinafter, the present invention will be described in more detail.

The present invention relates to an antimicrobial composition including phytic acid and electrolytes, and a disinfection method using the same.

The inventors of the present invention have experimentally identified that, when phytic acid or an electrolyte are mixed with each other under a condition in which each single composition does not exhibit bactericidal activity at all or exhibits slight bactericidal activity, bactericidal activity of the individual materials is maximized inducing the killing of acid resistant EHEC within 1 minute and within 5 minutes to a irreparable level, and have completed the present invention.

In the present invention, the electrolyte may include one or more among sodium chloride, potassium chloride, calcium chloride, magnesium chloride, sodium sulfate, potassium sulfate, calcium sulfate and magnesium sulfate, but is not limited thereto. The electrolyte interacts with phytic acid showing a synergistic bactericidal effect. This is due to the fact that the phytic acid of the antimicrobial composition of the present invention forms a chelate with multivalent positively charged ions forming a cell outer membrane of EHEC, and causes damage to the cell outer membrane, and thereby inhibits cellular homeostasis by facilitating cell permeability of various positively charged ions (example: $Na^+$, $Ca^{2+}$, $Mg^{2+}$ and the like) and negatively charged ions (example: $Cl^-$, $SO_4^{2-}$) generated while the electrolyte is dissolved in water.

The antimicrobial composition of the present invention preferably includes the phytic acid in 0.2% by mass or greater and the electrolyte in 3.0% by mass or greater with respect to the total mass of the composition, and more preferably, may include the phytic acid in 0.2% by mass to 5.0% by mass and the electrolyte in 1.0% by mass to 5.0% b. The above-mentioned range is preferable since synergistic bactericidal effect generated within 5 minutes is very clear when mixing the phytic acid or the electrolyte compared to the bactericidal effect exhibited by each of the materials when individually used, and therefore, efficiency of antimicrobial composition production and effectiveness is capable of being maximized.

In the present invention, the bacteria to be disinfected may be food poisoning bacteria, and may be one or more among Campylobacter jejuni, Yersinia enterocolitica, Cronobacter spp., Shigella spp., Vibrio spp., Escherichia coli O157:H7, Salmonella Typhimurium, Clostridium perfringens, Clostridium botulinum, Bacillus spp., Staphylococcus aureus, and Listeria monocytogenes, may preferably be Escherichia coli O157:H7, and may most preferably be EHEC O157:H7 (ATCC 35150, 43889, 43895).

In addition, the present invention includes a disinfection method treating the antimicrobial composition on bacteria to be disinfected.

Hereinafter, the present invention will be described in more detail with reference to examples. However, embodiments of the present invention described below are for illustrative purposes only, and the scope of the present invention is not limited to these embodiments. The scope of the present invention is shown in the appended claims, and moreover, includes all modifications within the meanings and the scopes equivalent to the descriptions in the claims. Hereafter, "%" means "% by mass."

Reference Example

Food Poisoning Bacteria to be Controlled

Based on the fact that phytic acid has very high acidity, EHEC O157:H7 (ATCC 35150, 43889, 43895), representative acid resistant food poisoning bacteria, was selected as bacteria to be tested, and in order to propose applicability of the developed technology more widely, bacteria cultured under a general environment (incubated in tryptic soy broth, 37° C., 24 hours: generally cultured bacteria) and cells having high acid resistance induced by acid adapted culture (incubated in 1% glucose-added tryptic soy broth, 37° C., 24 hours: acid adapted cultured bacteria) were prepared and used for the tests.

Test Example 1

Comparison on Bactericidal Activity of Phytic Acid or Aqueous Sodium Chloride Solution and Mixture Composition Thereof (Treated for 1 Minute)

Compositions of example and comparative examples were prepared by the concentrations of phytic acid and sodium chloride shown in the following Table 1. In other words, in order to compare bactericidal activity of each single composition of phytic acid or sodium chloride with bactericidal activity of a mixture composition thereof, a 50% aqueous phytic acid solution (Sigma-Aldrich Co. Llc., St. Louis, Mo., USA) and a 20% aqueous sodium chloride solution was prepared by dissolving 99.5% sodium chloride (Junsei Chemical Co., Ltd., Tokyo, Japan) in sterilized distilled water (DW) and used as an undiluted solution. This solution was diluted in sterilized DW in a proper ratio to prepare a 2% to 5% aqueous phytic acid solution and a 1% to 5% aqueous sodium chloride solution, and a mixture composition of phytic acid and sodium chloride was prepared by adding an undiluted phytic acid solution after preparing a 1% to 5% aqueous sodium chloride solution so that the final concentration became 2% to 5%.

The compositions of the examples and the comparative examples prepared as above were treated in each of the generally cultured bacteria and the acid adapted cultured bacteria of the reference example according to the following Table 1.

TABLE 1

| Test Group | Phytic Acid Concentration (%) | Sodium Chloride Concentration (%) | Treated Time (Minute) | Generally Cultured Bacteria | Acid Adapted Cultured Bacteria |
|---|---|---|---|---|---|
| Control Group (Single Composition) | — | 1-5 | 1 | Comparative Examples 1 to 5 | Comparative Examples 10 to 14 |
| | 2-5 | — | 1 | Comparative Examples 6 to 9 | Comparative Examples 15 to 18 |
| Test Group (Mixture Composition) | 2 | 1-5 | 1 | Examples 1 to 5 | Examples 21 to 25 |
| | 3 | 1-5 | 1 | Examples 6 to 10 | Examples 26 to 30 |
| | 4 | 1-5 | 1 | Examples 11 to 15 | Examples 31 to 35 |
| | 5 | 1-5 | 1 | Examples 16 to 20 | Examples 36 to 40 |

Figure 2:
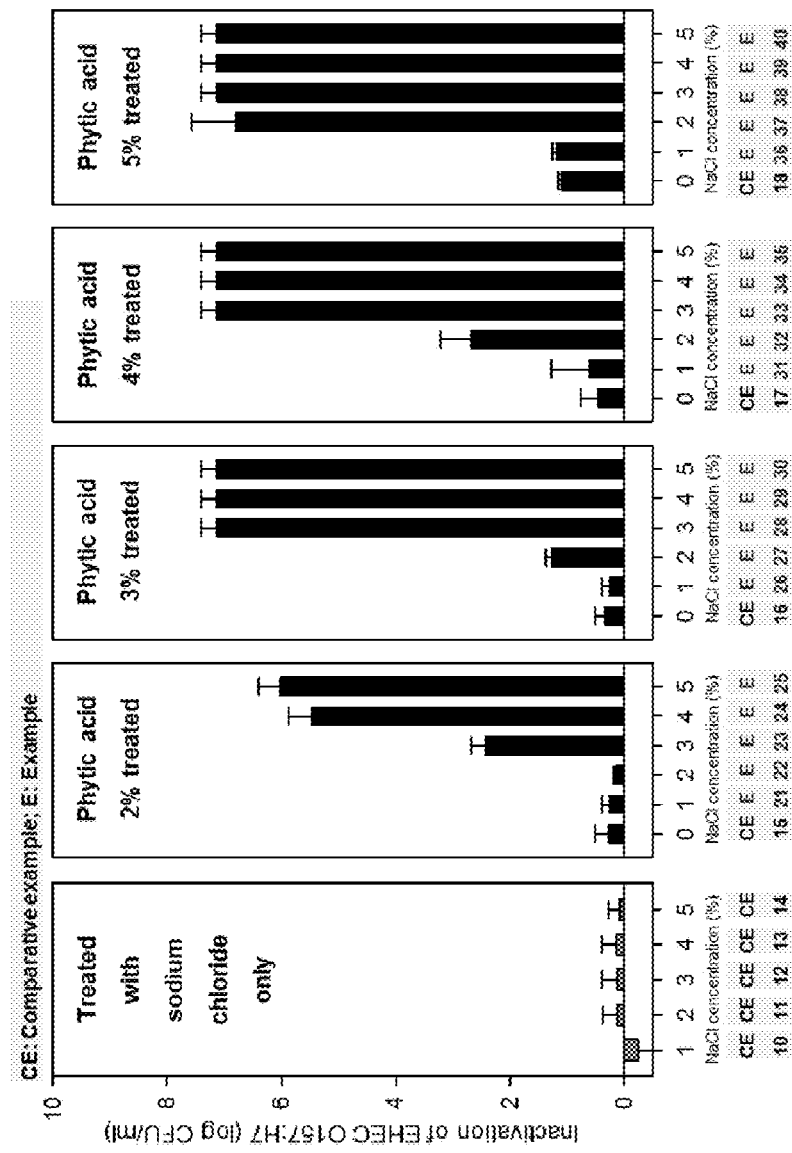
FIG. 2 shows comparison of bactericidal activity of phytic acid or an aqueous sodium chloride solution, and a mixture composition thereof (treated for 1 minute)

All the tests were repeated 3 times, and the results of Test Example 1 are shown in FIG. 1 and FIG. 2.

From the test results, it was seen that Examples 1 to 20 had a significantly high reduction effect compared to Comparative Examples 1 to 9, and particularly, Examples 3 to 5 and 8 to 10 adding 3% or greater of sodium chloride to 3% or less of phytic acid, and Examples 12 to 25 and 17 to 20 adding 2% or greater of sodium chloride to 4% or greater of phytic acid had a significantly increased reduction effect, and controlled the inoculated food poisoning bacteria to be controlled to a irreparable level.

In the case of acid adapted cultured bacteria having relatively higher acid resistance, Comparative Examples 10 to 18 had a significantly low reduction effect compared to the generally cultured bacteria, and it was identified that the pattern of the reduction effect increase shown in Examples 21 to 40 was clearer compared to the comparative examples. As for the reduction effect, Examples 23 to 25 and 28 to 30 adding 3% or greater of sodium chloride to 3% or greater of phytic acid, and Examples 32 to 35 and 37 to 40 adding 2% or greater of sodium chloride to 4% or greater of phytic acid had a significantly increased reduction effect as in the results with the generally cultured bacteria, and it was identified that the inoculated food poisoning bacteria to be controlled were controlled to a irreparable level.

Test Example 2

Comparison on Bactericidal Activity of Phytic Acid or Aqueous Sodium Chloride Solution and Mixture Composition Thereof (Treated for 5 Minutes)

Using the same method described in Test Example 1, compositions of example and comparative examples were prepared by the concentrations of phytic acid and sodium chloride shown in the following Table 2. In other words, an aqueous phytic acid solution, an aqueous sodium chloride solution, and a mixture composition of phytic acid and sodium chloride were prepared with the final concentration of the phytic acid being 0.2% to 1.0%.

The compositions of the examples and the comparative examples prepared as above were treated in each of the generally cultured bacteria and the acid adapted cultured bacteria of the reference example according to the following Table 2.

TABLE 2

| Test Group | Phytic Acid Concentration (%) | Sodium Chloride Concentration (%) | Treated Time (Minute) | Generally Cultured Bacteria | Acid Adapted Cultured Bacteria |
|---|---|---|---|---|---|
| Control Group (Single Composition) | — | 1-4 | 5 | Comparative Examples 19 to 22 | Comparative Examples 28 to 31 |
| | 0.2-1.0 | — | 5 | Comparative Examples 23 to 27 | Comparative Examples 32 to 36 |
| Test Group (Mixture Composition) | 0.2 | 1-4 | 5 | Examples 41 to 44 | Examples 61 to 64 |
| | 0.4 | 1-4 | 5 | Examples 45 to 48 | Examples 65 to 68 |
| | 0.6 | 1-4 | 5 | Examples 49 to 52 | Examples 69 to 72 |
| | 0.8 | 1-4 | 5 | Examples 53 to 56 | Examples 73 to 76 |
| | 1.0 | 1-4 | 5 | Examples 57 to 60 | Examples 77 to 80 |

Figure 3:
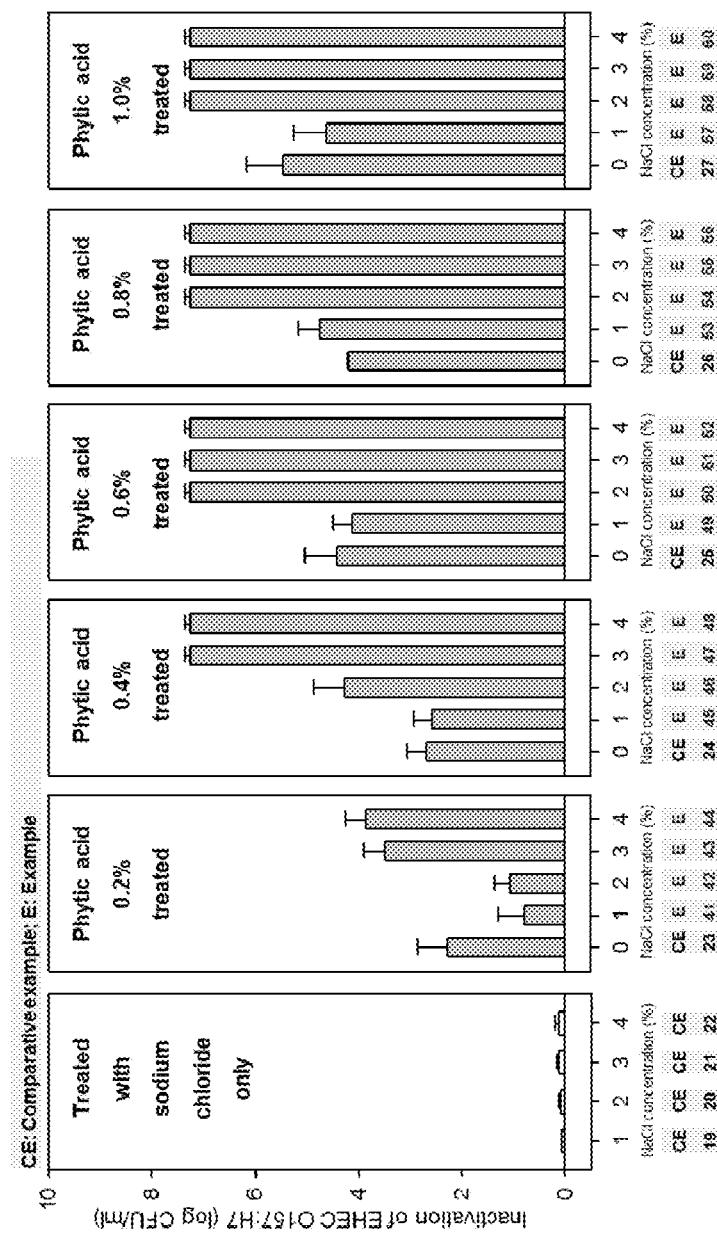
FIG. 3 shows comparison of bactericidal activity of phytic acid or an aqueous sodium chloride solution, and a mixture composition thereof (treated for 5 minutes)
Figure 4:
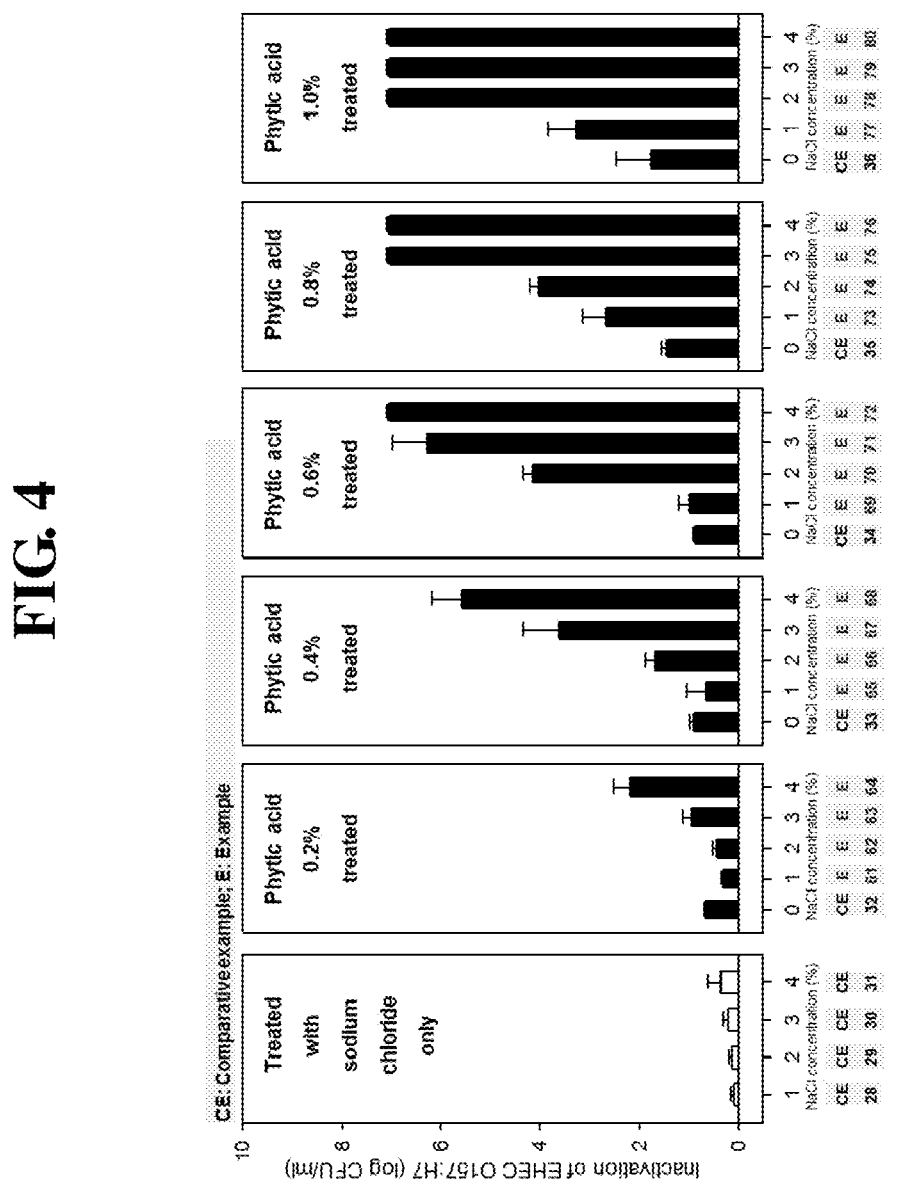

As in Test Example 1, all the tests were repeated 3 times, and the results of Test Example 2 are shown in FIG. 3 and FIG. 4. From the test results, it was seen that Examples 41 to 60 had a significantly high reduction effect compared to Comparative Examples 19 to 27, and particularly, Examples 47 and 48 adding 3% or greater of sodium chloride to 0.4% phytic acid had a significantly increased reduction effect.

In the case of acid adapted cultured bacteria having relatively higher acid resistance, Comparative Examples 28 to 36 had a significantly low reduction effect compared to the generally cultured bacteria, and it was identified that the pattern of the reduction effect increase shown in Examples 61 to 80 was clearer compared to the comparative examples. As for the reduction effect, it was identified that Examples 71, 72, and 75 to 76 adding 3% or greater of sodium chloride to 0.6% to 0.8% of phytic acid had a significantly increased reduction effect.

Test Example 3

Identification of Bactericidal Effect of Mixture Composition of Phytic Acid and Electrolyte Other Than Sodium Chloride In order to examine whether a phenomenon of a bactericidal effect increase of phytic acid with sodium chloride addition is maintained when electrolytes other than sodium chloride are used, Examples 4, 28, 29, 47 and 72, a minimum condition having a clear bactericidal effect increase of phytic acid by sodium chloride addition to kill the inoculated bacteria to a irreparable level, were selected, and potassium chloride, calcium chloride, and magnesium chloride were added in the same concentration and treated. The conditions are as shown in the following Table 3.

TABLE 3

| Comparable | Phytic Acid Concentration (%) | Electrolyte Concentration (%) | Treated Time (Minute) | Test Group of Electrolyte Mixture Composition |
|---|---|---|---|---|
| Example 4 | 2 | 4 | 1 | Comparative Examples 37 to 39 |
| Example 28 | 3 | 3 | 1 | Comparative Examples 40 to 42 |
| Example 47 | 0.4 | 3 | 5 | Comparative Examples 43 to 45 |
| Example 72 | 0.6 | 4 | 5 | Comparative Examples 46 to 48 |

As shown in the results of the following Table 4, it was seen that, in Comparative Examples 37 to 48, the generally cultured bacteria (Comparative Examples 37 to 39 and 43 to 45) and the acid adapted cultured bacteria (Comparative Examples 40 to 42 and 46 to 48) inoculated to the mixture composition were all killed as shown in the following Table 4, and it was identified that, the primary synergistic bactericidal effect of the present invention was also maintained when electrolytes other than sodium chloride were used.

TABLE 4

| | | | Reduction Effect (log CFU/ml) | | | |
|---|---|---|---|---|---|---|
| Phytic Acid Concentration (%) | Electrolyte Concentration (%) | Treated Time (Minute) | Sodium Chloride (Examples 4, 28, 47, 72) | Potassium Chloride (Comparative Examples 37, 40, 43, 46) | Calcium Chloride (Comparative Examples 38, 41, 44, 47) | Magnesium Chloride (Comparative Examples 39, 42, 45, 48) |
| 2 | 4 | 1 | 7.42 ± 0.03 | 7.42 ± 0.03 | 7.42 ± 0.03 | 7.42 ± 0.03 |
| 3 | 3 | 1 | 7.10 ± 0.11 | 7.10 ± 0.11 | 7.10 ± 0.11 | 7.10 ± 0.11 |
| 0.4 | 3 | 5 | 7.42 ± 0.03 | 7.42 ± 0.03 | 7.42 ± 0.03 | 7.42 ± 0.03 |
| 0.6 | 4 | 5 | 7.10 ± 0.11 | 7.10 ± 0.11 | 7.10 ± 0.11 | 7.10 ± 0.11 |

Test Example 4

Identification of Bactericidal Effect of Mixture Composition of Sodium Chloride and Organic Acid Other Than Phytic Acid In order to prove that a phenomenon of a bactericidal effect increase of phytic acid with sodium chloride addition is specific to phytic acid, a bactericidal effect was compared with cases using organic acids other than phytic acid. Examples 4, 28, 29, 47 and 72, a minimum condition having a clear bactericidal effect increase of phytic acid by sodium chloride addition to kill the inoculated bacteria to a irreparable level, were selected, and acetic acid (Comparative Examples 49, 53, 57 and 61), citric acid (Comparative Examples 50, 54, 58 and 62), lactic acid (Comparative Examples 51, 55, 59 and 63) and malic acid (Comparative Examples 52, 56, 60 and 64) were added in the same concentration and treated. The conditions are as shown in the following Table 5.

TABLE 5

| Comparable | Organic Acid Concentration (%) | Sodium Chloride Concentration (%) | Treated Time (Minute) | Test Group of Other Organic Acid Mixture Composition |
|---|---|---|---|---|
| Example 4 | 2 | 4 | 1 | Comparative Examples 49 to 52 |
| Example 28 | 3 | 3 | 1 | Comparative Examples 53 to 56 |
| Example 47 | 0.4 | 3 | 5 | Comparative Examples 57 to 60 |
| Example 72 | 0.6 | 4 | 5 | Comparative Examples 61 to 64 |

Figure 5:
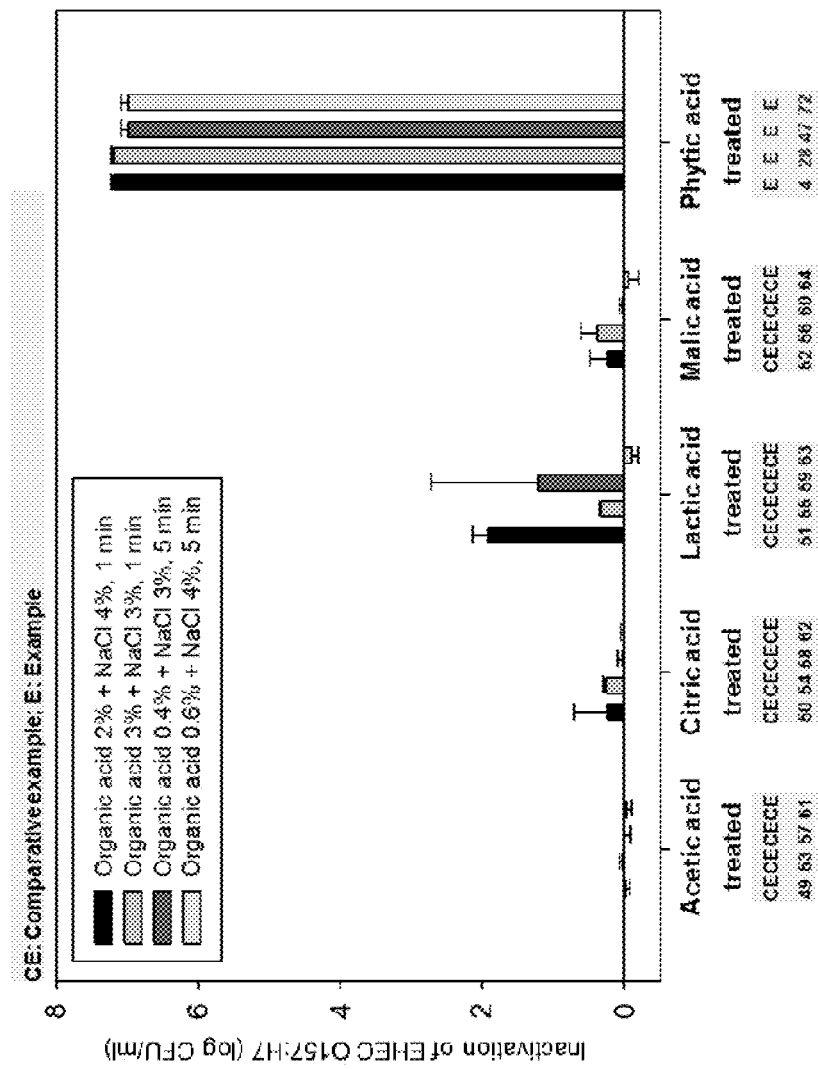
FIG. 5 shows a bactericidal effect of a mixture composition of phytic acid and sodium chloride compared to organic acids other than phytic acid.

As shown in the results of FIG. 5, it was seen that, in Examples 4, 28, 47 and 72, all the innoculated generally cultured bacteria (Example 4 and Example 47) and the acid adapted cultured bacteria (Examples 28 and 72) were killed, however, a reduction effect in the comparative examples was mostly 1 log CFU/ml or less, and 2 log CFU/ml or less even with the lactic acid, and it was identified that the primary synergistic bactericidal effect of the present invention was more clearly exhibited by phytic acid and not by other organic acids.

Test Example 5

Bactericidal Effect of Phytic Acid or Aqueous Sodium Chloride Solution and Mixture Composition Thereof for Bacteria Protected by Surface-Formed Biofilm In order to examine whether a phenomenon of a bactericidal effect increase of phytic acid by sodium chloride addition is also observed for bacteria protected by a surface-formed biofilm, a test was carried out after preparing a stainless steel (type 304) coupon (2×5 cm$^2$) normally used in various industrial fields, and then forming a biofilm.

First, the stainless steel coupon was immersed in 70% ethanol for 10 minutes, washed twice with sterile DW, and dried in a biosafety cabinet for 2 hours in order to prepare the sterilized stainless steel coupon. The dried coupon was again pressure sterilized for 15 minutes at 121° C., and used for the test. EHEC O157:H7 (ATCC 35150, 43889, 43895), representative acid resistance food poisoning bacteria used in Test Examples 1 to 4, was used as it is to form the biofilm, and as a minimum nutrient culture medium required for bacteria growth, an M9 culture medium known to form a more highly resistant biofilm was used. Generally cultured bacteria of each strain were diluted in a phosphate buffer solution to prepare a bacterial solution having an initial concentration of $10^7$ to $10^8$ CFU/ml, and then the sterilized coupon was placed therein so that the bacteria are attached to the coupon surface for 24 hours under a refrigerated environment (4° C.).

The coupon having bacteria attached on the surface was rinsed again for 5 seconds using sterile DW, then transferred to a sterile M9 culture medium, and cultured for 6 days at room temperature (22° C.) to form a biofilm. The biofilm-formed coupon was taken out from the culture medium using sterile forceps, rinsed for 5 seconds using sterile DW to remove bacteria remaining without being properly attached to the coupon surface and the biofilm, and then used for the test.

In order to verify bactericidal activity of the developed composition for bacteria protected by the biofilm, compositions of examples and comparative examples were prepared by the concentrations of phytic acid and sodium chloride shown in the following Table 6, and then the compositions were treated on the surface-formed biofilm prepared above for 5 minutes.

TABLE 6

| Test Group | Phytic Acid Concentration (%) | Sodium Chloride Concentration (%) | Treated Time (Minute) | Biofilm |
|---|---|---|---|---|
| Control Group (Single Composition) | 0-0.4 | — | 5 | Comparative Example 65 to 68 |
| | — | 1-4 | 5 | Comparative Examples 69 to 72 |
| Test Group (Mixture Composition) | 0.1 | 1-4 | 5 | Examples 81 to 84 |
| | 0.2 | 1-4 | 5 | Examples 85 to 88 |
| | 0.4 | 1-4 | 5 | Examples 89 to 92 |

Figure 6:
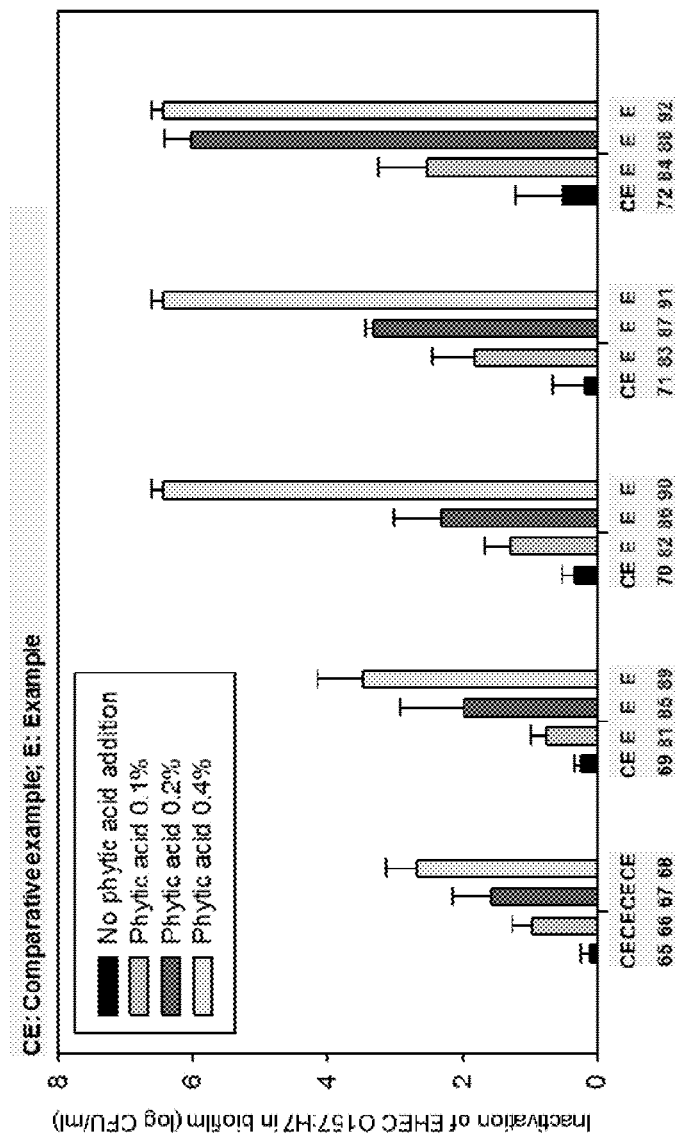
FIG. 6 shows a bactericidal effect of phytic acid or an aqueous sodium chloride solution, and a mixture composition thereof for bacteria protected by a surface-formed biofilm.

All the tests were repeated 3 times, and the results of Test Example 5 are shown in FIG. 6.

From the test results, it was seen that Examples 81 to 92 had an increased reduction effect compared to Comparative Examples 65 to 72, and particularly Examples 90 to 92 adding 2% or greater of sodium chloride to 0.4% or greater of phytic acid had a significantly increased reduction effect, and in Example 92, it was identified that the inoculated food poisoning bacteria to be controlled were controlled to a irreparable level.

According to the present invention, a natural antimicrobial agent capable of being utilized in food processing establishments, food service establishments and a food service industry can be manufactured and sold using an efficient antimicrobial composition capable of maximizing bactericidal power while using phytic acid in the minimum quantity.

What is claimed is:

1. A disinfection method comprising treating food poisoning bacteria with an antimicrobial composition comprising phytic acid and one or more electrolytes selected from the group consisting of sodium chloride, potassium chloride, calcium chloride and magnesium chloride; and wherein the food poisoning bacteria is one or more among *Campylobacter jejuni, Yersinia enterocolitica, Cronobacter* spp., *Shigella* spp., *Vibrio* spp., *Escherichia coli* 0157:H7, *Salmonella typhimurium, Clostridium perfringens, Clostridium botulinum, Bacillus* spp., *Staphylococcus aureus*, and *Listeria monocytogenes*; and wherein the antimicrobial composition comprises, with respect to a total mass of the composition, 0.2% to 5.0% by mass of the phytic acid and 1.0% to 5.0% by mass of the electrolyte.

* * * * *